US012708794B2

(12) United States Patent
Schultheis et al.

(10) Patent No.: US 12,708,794 B2
(45) Date of Patent: Aug. 18, 2026

(54) ILLUMINATION SYSTEM COMPRISING A LIGHT GUIDE HAVING A DIFFUSER ELEMENT

(71) Applicant: SCHOTT AG, Mainz (DE)

(72) Inventors: Bernd Schultheis, Schwabenheim (DE); Lothar Willmes, Destrich-Winkel (DE); Oliver Keiper, Huenstetten (DE); Hubertus Russert, Jugenheim (DE); Jonas Grimm, Bad Schwalbach (DE); Juergen Meinl, Hohenstein (DE); Martin Cramer, Wiesbaden (DE)

(73) Assignee: SCHOTT AG, Mainz (DE)

( * ) Notice: Subject to any disclaimer, the term of this patent is extended or adjusted under 35 U.S.C. 154(b) by 631 days.

(21) Appl. No.: 17/932,375

(22) Filed: Sep. 15, 2022

(65) Prior Publication Data

US 2023/0087914 A1 Mar. 23, 2023

(30) Foreign Application Priority Data

Sep. 15, 2021 (DE) ..................... 10 2021 123 831.5

(51) Int. Cl.
*G02B 6/02* (2006.01)
*A61N 5/067* (2006.01)
(Continued)

(52) U.S. Cl.
CPC ...... *A61N 5/067* (2021.08); *A61B 2018/2261* (2013.01); *A61B 2018/2277* (2013.01);
(Continued)

(58) Field of Classification Search
CPC .. A61N 5/00; A61N 5/067; A61N 2005/0651; A61N 2005/0665;
(Continued)

(56) References Cited

U.S. PATENT DOCUMENTS 5,219,346 A 6/1993 Wagnieres
5,401,270 A 3/1995 Mueller
(Continued)

FOREIGN PATENT DOCUMENTS

CN 103917902 7/2014
CN 106066511 11/2016
(Continued)

OTHER PUBLICATIONS

Cramer et al., Machine Translation of WO 2019063799 A1, Apr. 4, 2019. (Year: 2019).*
(Continued)

*Primary Examiner* — Jennifer Doan
(74) *Attorney, Agent, or Firm* — Ruggiero McAllister & McMahon LLC

(57) ABSTRACT

An illumination system for a medical technology therapy and/or diagnosis system is provided. The system includes a light source, preferably a laser light source, and a light guide, which at a proximal end can be connected to the at least one light source and/or can be assigned thereto, and which system has at the distal end of the light guide a diffuser element having a longitudinal axis which extends into or in the diffuser element perpendicularly with respect to an input face of the light guide, wherein the diffuser element emits light laterally with respect to the longitudinal axis over its active length in the operating state, wherein the diffuser element has at least one diffuser base body and the diffuser base body contains a matrix that has at least one scattering element and is enclosed at least on its cladding surface by a solid encapsulation.

18 Claims, 5 Drawing Sheets

(51) Int. Cl.
*A61B 18/22* (2006.01)
*A61N 5/06* (2006.01)

(52) U.S. Cl.
CPC ................. *A61N 2005/0651* (2013.01); *A61N 2005/0665* (2013.01)

(58) Field of Classification Search
CPC ............ A61N 5/062; A61N 2005/0602; A61N 2005/063; G02B 5/00; G02B 6/00; G02B 5/0242; G02B 6/3624; G02B 6/001; G02B 6/02; A61B 18/00; A61B 2018/2261; A61B 2018/2277
See application file for complete search history.

(56) References Cited

U.S. PATENT DOCUMENTS

| | | | | |
|---|---|---|---|---|
| 5,431,647 | A | 7/1995 | Purcell, Jr. | |
| 5,536,265 | A | 7/1996 | van den Bergh | |
| 5,989,246 | A | 11/1999 | Kaufmann | |
| 6,270,492 | B1 | 8/2001 | Sinofsky | |
| 6,810,184 | B2 | 10/2004 | Skutnik | |
| 2009/0204111 | A1 | 8/2009 | Bissig | |
| 2011/0040357 | A1 | 2/2011 | Arai | |
| 2012/0109264 | A1 | 5/2012 | Frangineas | |
| 2013/0088888 | A1 | 4/2013 | Fewkes | |
| 2013/0314940 | A1 | 11/2013 | Russert | |
| 2014/0376868 | A1 | 12/2014 | Ritter | |
| 2015/0016140 | A1 | 1/2015 | Weingärtner | |
| 2016/0313506 | A1 | 10/2016 | Agonoglu | |
| 2018/0092513 | A1 | 4/2018 | Melsheimer | |
| 2018/0299614 | A1 | 10/2018 | Schwagmeier | |
| 2020/0222712 | A1* | 7/2020 | Schultheis | ............ A61B 18/20 |
| 2021/0318494 | A1 | 10/2021 | Schultheis | |

FOREIGN PATENT DOCUMENTS

| | | | |
|---|---|---|---|
| DE | 10129029 | 12/2002 | |
| DE | 69526998 | 12/2002 | |
| DE | 102012100233 | 7/2013 | |
| DE | 102012208810 | 11/2013 | |
| DE | 102013208838 | 3/2015 | |
| DE | 102015119875 | 12/2016 | |
| DE | 102018133338 | 6/2020 | |
| EP | 0437183 | 7/1991 | |
| EP | 1527798 | 5/2005 | |
| EP | 2062077 | 5/2009 | |
| EP | 3184885 | 6/2017 | |
| WO | 9325155 | 12/1993 | |
| WO | WO-9607451 A2 * | 3/1996 | ............... A61L 2/10 |
| WO | 9607451 | 5/1996 | |
| WO | 2008024397 | 2/2008 | |
| WO | 2019063799 | 4/2019 | |
| WO | WO-2019063799 A1 * | 4/2019 | ............ A61B 18/20 |

OTHER PUBLICATIONS

Finlay, "In vivo determination of the absorption and scattering spectra of the human prostate during photodynamic therapy", Proc. SPIE Int. Soc. Opt. Eng. Jun. 14, 2014; 5315: pp. 132-142.

* cited by examiner

ILLUMINATION SYSTEM COMPRISING A LIGHT GUIDE HAVING A DIFFUSER ELEMENT

CROSS REFERENCE TO RELATED APPLICATIONS

This application claims benefit under 35 USC § 119 of German Application 10 2021 123 831.5 filed Sep. 15, 2021, the entire contents of which are incorporated herein by reference.

BACKGROUND

1. Field of the Invention

The invention relates to an illumination system, in particular for a medical technology therapy and/or diagnosis system, and to a method for producing a diffuser base body having a solid encapsulation, in particular for an illumination system, and to a method for structuring at least partially or in sections, in particular for adapting the intensity profile of the lateral emission, of a diffuser base body. The illumination system in this case comprises a light guide and a diffuser element having a solid encapsulation.

2. Description of Related Art

Such illumination systems are increasingly being used in the medical field. Currently, the following major applications may be categorized: photodynamic therapy (PDT) or photoimmunotherapy (PIT) for tumor therapy; endovenous laser therapy (EVLT) for treating varicose veins; laser-induced interstitial thermotherapy (LITT); and other applications, inter alia in the field of dental medicine, ophthalmology and dermatology.

Photodynamic therapy (PDT) is a minimally invasive therapy option for various cancer diseases. PDT refers to a method for treating tumors and other tissue modifications (for example vascularizations) with light in combination with a light-activatable substance. At the start of the treatment, light-sensitive substances, so-called photosensitizers, are injected intravenously into the patient's bloodstream, and these accumulate in or on the cancer cells. These natural photosubstances become concentrated in the tumor cells and give rise to a high photosensitivity there. For this purpose, a plurality of cannulas (typically up to 8), into each of which a light guide having a diffuser element is introduced, are inserted into the tumor tissue during the PDT treatment, the diffuser elements needing to be arranged distributed as spatially as possible over the tumor tissue. Laser light, generally with wavelengths in the visible spectral range, for example green light with a wavelength of 532 nm or red light with a wavelength of 690 nm, is coupled through the light guides into the diffuser elements so that the tumor tissue is illuminated as uniformly as possible from the inside. In this case, aggressive oxygen radicals which selectively destroy the tumor cells are formed in these cells. In contrast to the diseased cells, the healthy cells remain unaffected by this chemical reaction. The precise action mechanism is described, inter alia, in "Photodynamic Therapy of Cancer", Cancer Medicine, 2003.

In photoimmunotherapy (PIT), on the other hand, an immune response on or in the cancer cell, which under irradiation with light leads to the death of the cancer cell, is triggered with correspondingly modified photosensitizer.

A distinction is made here between cylindrical diffusers with typical active lengths of from 10 to 50 mm, spot diffusers which generate a forwardly directed illumination cone, and point radiators which have radial light emission.

In cylindrical diffusers, in particular maximally homogeneous lateral emission of the diffuser elements over their length in the operating state is important. This applies both axially, i.e. the emission intensity is the same in the scope of the homogeneity requirement at all points on any line from the proximal to the distal end in the direction of the longitudinal axis, and radially, i.e. the emission intensity is likewise the same in the scope of the homogeneity requirement at all points of any circumferential line along the longitudinal axis, so that these diffusers act almost as Lambertian emitters.

At the same time, a high scattering efficiency must also be achieved in order as far as possible to ensure a low heat input into the tissue. Typical homogeneity requirements for the lateral emission are a deviation of at most ±10 to 20% from the average intensity, it being necessary to avoid a forwardly directed emission, in particular from the distal end, of more than 10% of the light coupled in, typically at most 5%. The typical laser power in PDT applications is <5 W of continuous power, so that at most between 100 mW and 1000 mW, typically between 200 mW and 500 mW, are emitted per cm of diffuser length. This currently allows the use of plastic-based diffuser approaches.

Documents EP 2062077 A4, US 2009/0204111 A1 and DE 102015119875 A1 describes diffusers having a fiber.

Document EP 2062077 A4 or WO 2008/024397 A2 describes inter alia a diffuser for the output of optical energy with a high power density to a treatment site at the distal end of at least one optical fiber. A diffuser comprising a section of a predetermined length at the distal end of an optical fiber and scattering centers, which are positioned in the section of the predetermined length, is proposed, the scattering centers causing a part of the optical energy introduced to emerge radially onto a treatment site. The scattering centers may be scattering particles which are contained in the core or the encapsulation of the core. Besides complicated and difficultly controllable introduction in respect of, for example, the distribution and/or size of the nanocracks or nanocavities they may also have a negative effect on the fracture susceptibility of the component. It is furthermore necessary to take into account the fact that lateral emission cannot be achieved with the required homogeneity because of the exponential decrease of the lateral emission or nonuniform distributions.

Advantages would be offered here by a cylindrical diffuser such as is used in PDT applications. In EVLT treatment, however, much higher laser powers are required. For instance, the laser power is typically between 10 and 50 W at wavelengths in the NIR range, i.e. between about 800 nm and 1480 nm, which is currently provided by diode lasers (for example 810 nm, 940 nm or 1480 nm) or Nd:YAG lasers (1064 nm).

To date, longer wavelengths of around 2 μm have also become established for EVLT treatment. Then, for example, Tm:YAG lasers (1.9 μm) and Ho:YAG lasers (2.1 μm) are employed. Because of the absorption properties of tissue, lower laser powers, typically <10 W, are required at these wavelengths. Here, however, quartz glass light guides are already necessarily used in particular for the delivery of the laser light.

The homogeneity requirements for the lateral emission of diffusers that may be used for EVLT are not very high compared with a PDT application, and may be a deviation of at most ±30% to at most ±50% from the average intensity.

LITT is a minimally invasive method which is used for local tumor destruction. In this case, under imaging control (for example sonography/MRT), the tumor is punctured, one (or more) laser fiber(s) are introduced into the tumorous lesion and the latter is obliterated by thermal energy. In particular, Nd:YAG lasers (1064 nm), semiconductor lasers (980 nm) and diffuser tip applicators are employed here. The laser power is about 5 to 8 W (see inter alia "Laserinduzierte Interstitielle Thermotherapie (LITT) bei malignen Tumoren" [Laser-induced interstitial thermotherapy (LITT) for malignant tumors], BÄK and KBV January/2002).

Document WO 2019/063799 A1 in the name of the Applicant describes an illumination system having a light guide and a diffuser element, as well as a method for producing and/or for structuring a diffuser base body at least partially or in sections, which already enables high homogeneity requirements for the lateral emission of diffusers.

The described diffuser base body comprises a light guide and devices for homogenizing the emission intensity along the longitudinal axis of the diffuser base body. It is possible to achieve an intensity distribution of the lateral emission which deviates by at most ±50%, preferably at most ±30% and most preferably at most ±5% from the average lateral emission intensity.

As has been shown by measurements of a multiplicity of cylindrical diffusers constructed or produced in this way, good homogeneity values in the emission characteristic and high efficiency values, such as are necessary for the applications described in the introduction, can already be achieved in this way.

However, it has also been found that back-scattering effects may occur, particularly with certain power values of the laser radiation or of the light.

For instance, light may be scattered back into the light guide, in which case it may even reach the laser light source. This may lead to undesired light phenomena in the light guide. In addition, depending on the level of the intensity of the back-scattered light, the laser light source may become unstable, which may lead to it then possibly being turned off.

Furthermore, hotspots, at which an undesired temperature rise of the illumination system may take place, may locally occur as a result of the back-reflection. In particular applications, this is undesired and may negatively affect a treatment.

SUMMARY

It is therefore an object of the invention to minimize the aforementioned disadvantages while further increasing or at least maintaining the high homogeneity and efficiency.

The object of the invention is achieved by the subject matter and advantageous refinements of the description and the drawings.

For this purpose, an illumination system, in particular for a medical technology therapy and/or diagnosis system, is proposed, comprising at least one light source, in particular a laser light source, and a light guide, which at a proximal end can be connected and/or is connected to the at least one light source, and which system has at the distal end of the light guide a diffuser element having a longitudinal axis which extends into the diffuser element perpendicularly with respect to an input face of the light guide, wherein the diffuser element emits light laterally with respect to the longitudinal axis over its active length in the operating state, wherein the diffuser element has at least one diffuser base body which comprises a matrix that has at least one scattering element and is enclosed at least in sections on its cladding surface by a solid encapsulation, and wherein the solid encapsulation is configured with a multipart or multilayer structure comprising at least two encapsulating tubes or layers, preferably at least three encapsulating tubes or layers.

The light source may comprise a laser light source or semiconductor-based light source or light-emitting diode (LED), in particular also a laser diode (LD), or a laser.

The diffuser base body is accordingly, in a preferred embodiment of the invention, at least partially or in sections or preferably also fully enclosed or enclosable on its cladding face by a solid encapsulation, in which case this solid encapsulation may in a preferred embodiment of the invention be a sequence of encapsulating tubes. The encapsulating tubes may have different optical properties.

The solid encapsulation may, however, also comprise a multilayer or multicomponent or multipart structure, that is to say at least one layer which may be applied on an encapsulating tube or between encapsulating tubes. Accordingly, a solid encapsulation may comprise two encapsulating tubes. In addition, the solid encapsulation may comprise a layer and/or a further encapsulating tube or a different combination of encapsulating tubes and/or layers, in particular at least three, preferably three, successive encapsulating tubes.

The illumination system according to the invention may furthermore be characterized by at least one of the following features:

- the at least one scattering element is arranged along the longitudinal axis of the diffuser base body while being aligned substantially parallel thereto or at an angle with respect to the longitudinal axis,
- at the distal end of the diffuser base body and/or at the transition region between the light guide and the diffuser base body and/or at the diffuser base body, devices enclosing the latter at least partially or in sections are provided for homogenizing the emission intensity along the longitudinal axis of the diffuser base body,
- the diffuser base body has at its distal end a reflector face with which light passing through the diffuser base body can be reflected back at least partially during operation, and/or
- the illumination system has in the operating state an intensity distribution of the lateral emission which deviates by at most ±50%, preferably at most ±30% and most preferably at most ±5% from the average lateral emission intensity.

The average lateral emission intensity in this case means the average value of the lateral emission intensity as measured over the length of the diffuser base body.

In the context of the present disclosure, lateral emission is intended to mean emission which has direction components that extend in the radial direction starting from the longitudinal axis of the diffuser base body. A lateral emission intensity is intended to mean the intensity of this emission.

Back-reflected light is intended to mean radiation which is reflected back by the reflector face at the distal end of the diffuser base body into the latter, in which case light may also be guided through the solid encapsulation or the encapsulating tube.

The at least one scattering element may be arranged along the entire longitudinal axis of the diffuser base body with a uniform cross section, substantially parallel thereto or, in the case of tapering diffuser base bodies, at an angle with respect to the longitudinal axis. The at least one scattering element may advantageously also be tubular and, in particular, arranged coaxially with respect to the longitudinal axis.

Scattering areas which are arranged around the longitudinal axis of the diffuser base body, in particular along it, are also conceivable. According to one embodiment, the scattering area or areas wind spirally around the longitudinal axis of the diffuser base body. Embodiments in which the scattering element or the scattering region are arranged with a constant pitch around the longitudinal axis of the diffuser base body have proven to be particularly advantageous. In this case, the scattering region may be in the form of a helix that winds around the longitudinal axis of the diffuser base body.

The individual scattering regions may be formed by one or more scattering elements. One embodiment provides that the scattering region is formed by a scattering element in the form of a helix or spiral. Such scattering element or scattering area arrangements in the base body have the advantage that an increased scattering interaction with axis-parallel light components or for light components which run at a small angle to the diffuser axis can take place and thus the scattering efficiency can be increased. In addition, the homogeneity of the radiation can be optimized.

A multiplicity of scattering elements may be arranged in a particular predeterminable geometrical arrangement around the longitudinal axis of the diffuser base body, preferably in a regular structure around the latter, particularly preferably circularly. A multiplicity of scattering elements arranged at an angle therefore preferably meet at a vanishing point outside the diffuser base body.

At the distal end of the diffuser base body, the transition region between the light guide and the diffuser base body, devices and/or measures for homogenizing the lateral emission along the longitudinal axis are preferably provided, which enclose the diffuser base body at least partially or in sections and/or substantially completely.

For example, the devices include sleeves, encapsulations, caps and/or layers at the distal end of the diffuser, in order to prevent forwardly directed emission from the distal end or to reflect it back and therefore provide it again for the scattering processes in the diffuser base body, and on the other hand to prevent scattered light effects and/or light reflections at the distal end of the diffuser base body.

The same applies for the transition region between the light guide and the diffuser base body. Here as well, scattered light effects and/or light reflections may occur, which may be reduced by correspondingly acting elements, for example sleeves and/or layers at this position.

The light guide may comprise an individual fiber, for example a single-mode or multimode light guide fiber, comprising a core having a core diameter and a cladding, or a fiber bundle having a fiber bundle diameter.

Diffuser elements for medical therapies such as are mentioned in the introduction, which emit homogeneously in the operating state, may therefore be provided reproducibly and also in a cost-optimized fashion.

According to one preferred embodiment variant, it is provided that the scattering elements in the diffuser base body are arranged radially distributed uniformly around the longitudinal axis of the diffuser base body, a core zone having no scattering elements or a significantly reduced number of scattering elements per unit area compared with the number of scattering elements per unit area outside the core zone about the longitudinal axis, and the scattering elements therefore being arranged predominantly outside this core zone in the matrix.

It is therefore possible to achieve the effect that the light coupled in, which is generally coupled in with a low NA (<0.3, typically around 0.2), is not immediately scattered at the scattering elements. On the other hand, because of the almost scattering element-free core zone, enough light can be guided without scattering as far as the distal end of the diffuser base body. In this way, on the one hand, the intensity close to the input position (proximal end of the diffuser base body) can be reduced, and on the other hand the intensity close to the distal end of the diffuser base body can be increased.

In another preferred embodiment variant, it can be provided that the diffuser base body has in relation to its cross-sectional area a matrix that has different refractive indices $n_1$ and $n_1'$, in particular between the core zone and the edge region of the matrix, in which the scattering elements are incorporated. In this way, for example, the numerical aperture NA may be influenced in the core zone with a matrix refractive index $n_1$ and outside the core zone of the matrix with a refractive index $n_1'$.

Furthermore, the propagation of the light in the diffuser base body and therefore excitation of the scattering centers over the length of the diffuser can thus be adapted to the required emission characteristic. Furthermore, any desired cross-sectional geometry of the core zone with the refractive index $n_1$, that is to say for example from substantially circularly round to a polygonal or star-like shape, may be produced in the production process.

The homogenization of the intensity of the lateral emission may be reinforced if the diameter of the diffuser base body in which the scattering elements are embedded, is equal to or greater than a core diameter or fiber bundle diameter of the light guide.

A ratio between the core diameter or fiber bundle diameter of the light guide and the diameter of the matrix of from ≤1.0 to 0.7, particularly preferably from ≤1.0 to 0.8, has been found to be particularly favorable.

A core diameter or fiber bundle diameter which is only slightly less than the diameter of the matrix may in this case reduce an intensity peak at the input position (transition region of the light guide and the diffuser base body).

A much smaller core diameter or fiber bundle diameter compared with the diameter of the matrix of the diffuser base body, that is to say a ratio of <0.8, may on the other hand lead to an intensity reduction at the input position, which may likewise be advantageous for particular requirements.

If the ratio is between 1 and 0.9, it has furthermore been found that a particularly robust mechanical coupling or connection, for example by means of splicing, may be achieved between the light guide and the diffuser base body.

In a preferred embodiment, the diffuser element has a connecting zone between the proximal end of the diffuser base body and the distal end of the light guide, which is produced with a form and/or material fit by means of adhesive bonding, splicing or pressing, and which connects at least the diameter of the diffuser base body and the core diameter or the fiber bundle diameter of the light guide.

In order to match possibly different thermal expansion coefficients, it may be advantageous for an intermediate medium additionally to be provided in the connecting zone between the proximal end of the diffuser base body and the distal end of the light guide. This may, for example, be a junction glass or a solder glass. On the other hand, it may also be a transparent permanently elastic adhesive. Furthermore, an optical element may be arranged in the connecting zone or the connecting zone may be configured as an optical element, in order for example to modify the beam guiding and/or light steering geometrically or by adaptation of refractive powers.

The diffuser base body may substantially consist of a matrix of transparent plastic, glass, quartz glass or glass ceramic, in which case the scattering elements incorporated therein may for example consist, in the case of a plastic ceramic, of a porous or pigmented or for example whitely colored plastic, in the case of a glass matrix of pores, particles, porous or pigmented or for example whitely colored or inhomogeneity-containing glass or glass ceramic elements and the crystallites contained therein, in the case of a quartz matrix of pores, porous quartz glass or ceramic or polycrystalline particles, or in the case of a transparent glass ceramic matrix of pores, particles, porous or pigmented or for example whitely colored or inhomogeneity-containing glass or glass ceramic elements and the crystallites contained therein.

In this case, combinations of the scattering elements mentioned by way of example may advantageously also be present in the respective matrix. The inhomogeneities of the glass or the glass ceramic, which may form the scattering elements in the case of glass or glass ceramic matrix solutions, comprise for example phase segregations, demixings and/or particulate incorporations, nuclei and/or crystallites.

In this case, the concentrations of the scattering elements in the scattering region should be from 10 ppm to 1000 ppm and preferably from 20 ppm to 100 ppm. In this case, the concentration specification in ppm refers to the proportion of the scattering particles in relation to the mass fractions of the constituents of the respective material, in particular the plastic, the glass matrix or the quartz matrix, in which the scattering particles are incorporated. In this case, the respectively formed scattering elements, which means for example the pores, particles, porous or pigmented or for example whitely colored or inhomogeneity-containing glass or glass ceramic elements and the crystallites contained therein, preferably have a diameter of from 10 nm to 1000 nm, particularly preferably from 100 nm to 800 nm.

A plastic-based solution approach for the diffuser base body consisting of plastic rods of for example PMMA, PET or PC may already be carried out at low process temperatures during its production or shaping. However, diffuser base bodies constructed in this way correspondingly have a rather low thermal stability and are therefore more suitable for applications with a low laser power. Furthermore, they are only suitable for applications in the visible spectral range (VIS) since plastics have a generally high absorption in the NIR or IR range.

Glass-based approaches are substantially more robust here, and above all thermally more stable, so that higher laser powers may also be applied. As elements for the construction of the diffuser base body, for example rods of the glasses of the type N-BK7, optical boron crown glass in the name of the Applicant, borosilicate glass or Pb- or heavy metal-free glass is envisaged, such as are used inter alia as core glass for optically high-quality glass fibers, for example for endoscopes or dental rods for curing tooth fillings. With the latter, future RoHS requirements may be satisfied. Such glasses are described in printed publications DE 10 2012 100 233 A1 and DE 10 2013 208 838 B4 in the name of the Applicant, which are fully incorporated here.

Examples of such glasses for the light guide rods or for the matrix of the diffuser base body from the range of lead-free tin silicate glasses or alkali zinc silicate glasses contain the following components (data in wt. % based on oxide):

| | from | to |
|---|---|---|
| $B_2O_3$ | 0 | 24 |
| $SiO_2$ | 23 | 62.1 |
| $Al_2O_3$ | 0 | 10 |
| $Li_2O$ | 0 | 10 |
| $Na_2O$ | 0 | 18.5 |
| $K_2O$ | 0 | 25.7 |
| BaO | 0 | 57.8 |
| ZnO | 0 | 40 |
| $La_2O_3$ | 0 | 25 |
| $ZrO_2$ | 0 | 10 |
| $HfO_2$ | 0 | 14.2 |
| $SnO_2$ | >0 | 2 |
| MgO | 0 | 8 |
| CaO | 0 | 8 |
| SrO | 0 | 24.4 |
| $Ta_2O_5$ | 0 | 22 |
| $Y_2O_3$ | 0 | 11.9 |
| $Rb_2O$ | 0 | 15 |
| $Cs_2O$ | 0 | 21 |
| $GeO_2$ | 0 | 7.5 |
| F | 0 | 2 |
| Σ $R_2O$ | 5 | 20 |
| Σ MgO, CaO, SrO, ZnO | 20 | 42 |

The encapsulating tubes are for example selected from one of the following Groups 1 to 4, which each contain the following components (data in wt. % based on oxide):

| | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | 0-2 | 0-1 | 0-3 | 0-2 |
| $Na_2O$ | 0-10 | 8-20 | 2-8 | 0-10 |
| $K_2O$ | 0-10 | 0-6 | 0-1 | 0-10 |
| MgO | 0-1 | 0-5 | 0 | 0-5 |
| CaO | 0-2 | 1-9 | 0 | 0-5 |
| SrO | 0-1 | 0 | 0 | 0-5 |
| BaO | 0-4 | 0-5 | 0 | 0-5 |
| F | 0-1 | 0-1 | 0 | 0-1 |
| Cl | 0-1 | 0-1 | 0 | 0-1 |
| $Fe_2O_3$ | 0-2 | 0-2 | 0-2 | 0-2 |

If the solid encapsulation now has a multilayer structure, or in particular at least two encapsulating tubes, it is in particular possible to achieve the effect that scattered, guided and reflected or back-reflected light components likewise contribute in a defined way to the lateral emission along the diffuser length.

This is already achieved particularly effectively with a structure having at least two encapsulating tubes, the inner, first encapsulating tube preferably being constructed from a transparent borosilicate glass and the subsequent, second encapsulating tube being constructed from a translucent scattering glass, in which scattering centers may be incorporated. These scattering centers may be particles, phase boundaries or demixings.

The second encapsulating tube may, in one particularly preferred embodiment, comprise a white glass. A white glass may comprise white pigments in order to achieve a whitish color impression.

A white glass encapsulation tube may according to one preferred embodiment be or comprise a preferably translucent silicate white glass. This may have an extreme scattering effect. It may for example be an As—Pb-containing silicate glass. Such a glass is a silicate glass which contains lead (Pb) and arsenic (As). Inhomogeneous regions in the glass, which may have an increased lead and/or arsenic content compared with the surrounding glass, may be used as a scattering element for the scattering. As an alternative, of course, scattering elements, for instance scattering particles, may also be incorporated and form the scattering centers.

In another likewise preferred embodiment of the invention, a further, third encapsulating tube is provided for the solid encapsulation. This third encapsulating tube may represent the outer encapsulating tube of the solid encapsulation. The first and the second encapsulating tubes may in this case be configured as mentioned above.

According to one embodiment, instead of a second cladding tube made of a glass with a high scattering center density, for example white glass, a ring of individual glass rods with a high scattering center density or of individual white glass rods can also be used. The glass rods arranged in a ring are placed between the first inner cladding tube and the third outer cladding tube. During the drawing process, the glass rods fuse together and form a homogeneous scattering layer. Due to the annular arrangement of the glass rods, this is essentially ring-shaped or tubular in form.

The effect very advantageously achievable with these configurations of the solid encapsulation is that only a very small proportion is returned through the coupling position to the light guide or into this light guide, or even further in the direction of the laser light source. In this way, it is very advantageously possible to ensure that no light or only a small proportion of the light, which is preferably less than 10% of the emitted light of the laser light source, even more preferably less than 5% of the emitted light, is scattered back again into the delivering light guide, or enters the latter.

It has been found favorable for at least two of the encapsulating tubes of the solid encapsulation to differ from one another in at least one optical property. The optical property in this context means, for example, properties in respect of the transparency or translucence, there being a corresponding difference, for example in the case of a clearly transparent encapsulating tube and a translucent encapsulating tube, of the refractive index and/or the material of the encapsulating tube.

In addition or as an alternative, a difference in an optical property may also mean a different transmission behavior of the corresponding encapsulating tubes, for instance the transmission behavior of electromagnetic radiation, preferably in the spectrum of the application wavelengths.

In addition or as an alternative, a difference in an optical property may also mean a difference in the value of the refractive index of the corresponding encapsulating tubes, for instance a difference in the value of the refractive index of for example about 0.05 or about 0.1.

A solid encapsulation, comprising for example at least three encapsulating tubes having different optical properties, may significantly further reduce the risk of undesired light phenomena in or on the light guide, in particular at also its ends or transition to the diffuser body. Furthermore, in this way it is also possible to prevent the light source from becoming unstable or even being turned off, so that greater safety is provided in the treatment. This applies in particular to laser light sources.

Also, local hotspots or other light phenomena, which may be induced for instance at the splice position, i.e. the transition from the light guide to the diffuser body, as a result of the back-reflection, in particular from the diffuser body to or into the light guide, may particularly advantageously be avoided. Therefore, undesired temperature rises of the illumination system, which may have an unfavorable effect on treatment and possibly also the procedure, may also be precluded. Damage to the patient and the operator is prevented or at least minimized.

A particularly suitable embodiment, in which the solid encapsulation comprises three encapsulating tubes, will be presented below.

In this embodiment of the invention, it has proven particularly advantageous for a first encapsulating tube, which directly encloses the matrix at least in sections, to be configured to be substantially clearly transparent and preferably to have a refractive index lower than the refractive index of the material of the matrix. Exemplary glasses and their composition are mentioned in the table above relating to the cladding glasses.

This first encapsulating tube may essentially represent the optical cladding of a diffuser body, so that the light coupled in is initially guided as far as the distal end of the diffuser base body and only the light scattered at the scattering elements at large angles with respect to the axis of the diffuser base body is laterally emitted.

Furthermore advantageously, a second encapsulating tube is provided, which encloses the first encapsulating tube at least in sections, and the second encapsulating tube preferably being configured to be translucent or scattering. In this case, the second encapsulating tube may have a refractive index higher than the refractive index of the first encapsulating tube.

If the second encapsulating tube is configured to be translucent or scattering and furthermore has a refractive index which is higher than that of the first encapsulating tube, it is possible to achieve the effect that the back-reflected light guided through the first encapsulating tube can likewise be scattered away outward in a defined way.

Furthermore, because of multiple scattering at or in this second encapsulating tube, further homogenization of the emitted light may be achieved. This also relates inter alia to the angle distribution, so that almost Lambertian emission may be achieved.

Furthermore advantageously, a third encapsulating tube is provided, which encloses the second encapsulating tube at least in sections, the third encapsulating tube preferably being configured to be substantially clearly transparent.

With a third encapsulating tube which is configured to be substantially clearly transparent, it is possible to achieve the effect that the structure is mechanically stabilized and a smooth, continuous surface is therefore also made possible.

Depending on the configuration of the second encapsulating tube, a third encapsulating tube may also be regarded as optional. This may apply when, as mentioned further above, the second encapsulating tube is also white glass or comprises white glass.

In one refinement of the invention, it can additionally be provided that the solid encapsulation comprises more than three encapsulating tubes, in which case a sequence as for example described above may be partly or fully repeated. However, the further encapsulating tubes may of course also be configured differently.

It is particularly advantageous in this case for the matrix having the at least one scattering element and the multilayer solid encapsulation, or solid encapsulation comprising a plurality of encapsulating tubes, to be configured as a continuous composite without cavities.

This means that, in particular, gap-free optical coupling takes place between the first and the second encapsulating tubes, preferably all the encapsulating tubes. That means that the respective walls of the encapsulating tubes preferably bear directly on one another or that there is no air, for instance air inclusions or air bubbles, between the encapsulating tubes. In other words, the side faces of neighboring encapsulating tubes have maximally full-area contact with one another. Here, in other cases undesired optical effects may thereby be induced, for example because of the resultant refractive index leaps.

If, as is provided by one particularly preferred embodiment of the invention, the diffuser element is formed with the matrix, at least one scattering element and a solid encapsulation which comprises encapsulating tubes consisting of glass, a particularly compact, dense diffuser base body without cavities may be provided. For this purpose, the encapsulating tubes of the encapsulation may be fused to form a compact, continuous body in a drawing process, as will be described further below.

In this way, it is possible to ensure that no liquid, which could negatively influence the emission behavior, can enter the illumination system according to the invention during use.

Furthermore, such a diffuser base body is also mechanically very stable. The latter may be achieved if the production is carried out in a drawing method, which will be discussed in more detail further below. In the case of a drawing method, the viscosity and the thermal expansion coefficient of the material of the encapsulating tubes may particularly favorably be selected and matched to one another in such a way that a compressive stress is induced after fusion of the components by the drawing process during cooling of the diffuser base body, for example to room temperature. Advantageously, the thermal expansion coefficient of the outermost encapsulating tube may in this case be selected in such a way that it lies at least somewhat above that of the adjacent inner encapsulating tube.

At least one of the encapsulating tubes, for example the third encapsulating tube, may be purposely selected as a function of the intended uses, in order to achieve particular optical properties.

Thus, in one refinement of the invention, for example an X-ray opaque glass can be selected for at least one encapsulating tube, for example the outer-lying encapsulating tube. This has the advantage that the diffuser base body as a whole is identifiable at least partially or in sections in an X-ray image. The position of the diffuser in the body of a patient may therefore be located in a particularly straightforward way.

In respect of application wavelengths of from 0.8 μm to about 2.2 μm, for example for the EVLT applications mentioned in the introduction, special IR-transparent glasses may also be used, such as for example are known under the designations N-PK52a, a phosphate crown glass, or IRG7, a lead silicate glass, with approx. 30 Gew.% PbO, from the Applicant. Such glasses with high Pb-contents also offer the advantage that they are appropriately conspicuous on X-ray images and can serve as X-ray markers.

Particularly effective use of the light radiated into the diffuser base body for the lateral emission may be achieved with a reflector face which terminates the diffuser base body at the distal end and/or at least partially or in sections comprises it on its circumferential face, and which reflects the light back directly and/or diffusely.

In this case, reflector faces which are formed as a sputtered or vapor-deposited dielectric reflection layer on the distal end of the diffuser base body and which consist of a plurality of layers and are matched in respect of the reflectivity to the wavelength of the light used, have proven favorable, a maximum of the reflectivity preferably being adjustable at this wavelength by the layer sequence and the respective layer thickness of the individual layers.

With such layers, a reflectivity of from >95% to >99.5% may be purposely adjusted.

Alternatively or in addition, in another embodiment of the invention, it can be provided for the reflector to be formed from a highly broadband-reflective coating, for example a silver layer, optionally with rear-side passivation or protective layer. These are particularly robust and can suppress perturbing reflections that may lead to local intensity elevations as well as hotspots. In this way, in particular, it is possible to produce a very broadband reflector which has very good reflection properties both in the visible spectral range (VIS) and in the IR/MIR range ("IR"=infrared, "MIR"=medium infrared), for example between a wavelength of 1 μm and 2.5 μm. A rear-side passivation prevents oxidation, for example of the silver layer.

In another embodiment variant, it may be provided that a first maximum of the reflectivity exists for a first wavelength, for example the wavelength of the light used, or the application wavelength, and at least one further, second maximum of the reflectivity also exists for at least one further wavelength. The at least one further wavelength may in this case advantageously differ from the application wavelength. Very advantageously, further functions may be integrated in this way.

In this case, the at least two maxima may in particular have a reflectivity of >95%, preferably >99%. In other words, a first maximum of the reflectivity may exist at a particular wavelength of the light of the light source and at least one further, second maximum of the reflectivity may exist at a further wavelength, in which case this wavelength may differ from the first wavelength of the light of the laser light source, and the reflectivity of the first maximum and that of the at least one further maximum preferably being >95%, preferably >99%. In order to generate light of the further wavelength, a further light source may for example be provided, for instance a further LED light source, which for example emits light with a lower power.

The term application wavelength in this case means the wavelength of electromagnetic radiation which is intended or selected for a particular treatment, for example 690 nm.

In this way, it is possible to avoid perturbing emissions at the distal end of the diffuser base body for the application wavelength, for example 690 nm, here meaning the treatment wavelength, and for another wavelength, for example that of a pilot light with for example green light, for example 500 nm to 550 nm, which is often used for setting up and for function control of the component.

According to another embodiment of the invention, it is provided that the reflector face is formed at least in sections at an angle of less than 90°, preferably between 85.0° and 89.9°, with respect to the longitudinal axis of the diffuser base body, and light reflected back during operation can be reflected with a larger numerical aperture NA than the light which impinges on the reflector face.

In this way, better use of the scattering elements incorporated in the diffuser base body may be achieved for the lateral light output, which is associated with a rise in efficiency but also with an increase in the homogeneity over the diffuser length.

In yet other embodiments, a concavely or convexly configured reflector face may be provided. Plane reflector faces simply formed obliquely with respect to the longitudinal axis of the diffuser base body or a faceted reflector face, which in sections has plane faces that have different angles with respect to the longitudinal axis of the diffuser base body, may also be particularly preferred in respect of the production process.

Despite the aforementioned measures, under certain circumstances a part of the light reflected back, particularly in the region of the transparent sleeve provided as mechanical reinforcement, at the transition between the diffuser base body and the light guide, may still be guided through this sleeve in the direction of the delivering light guide and/or into the latter, which on the one hand may cause undesired illumination of the light guide or else, for instance at a relatively high laser power, lead to undesired heating.

The transparent sleeve may be produced from plastic, glass, metal or ceramic material, or may comprise plastic, glass, metal or ceramic material. The plastic may, for example, be selected from the group of thermoplastics such as polycarbonate (PC). Glass offers advantages in relation to mechanical stability because of its E modulus.

Heating may also be generated in particular locally as a so-called hotspot because of local absorptions. Particularly if the light guided through the transparent sleeve impinges on the outer cladding (buffer) of the light guide, this leads to intensely pronounced light reflection and to local heating.

According to a particularly preferred embodiment of the invention, it is therefore provided, that a further translucent or partially absorbent encapsulation is provided in the region between the transparent sleeve and the outer cladding of the light guide.

This translucent or partially absorbent encapsulation may advantageously be formed from a polymer in which scattering particles are incorporated.

At least partial reduction of the light impinging on the outer cladding may therefore be achieved. Lateral emission may furthermore occur by multiple reflection in this encapsulation, although this is scarcely perceptible with the eye since it takes place uniformly over the entire length of this encapsulation and with a much lower power density, so that this lateral emission takes place while being significantly attenuated. Hotspots are thereby avoided.

In respect of the technical implementation, it has proven advantageous for the translucent or partially absorbent encapsulation to be a tubing section, a shrink tubing section and/or a re-coating polymer, into which scattering particles may be introduced beforehand if so desired.

The scope of the invention also includes a method for producing a diffuser base body according to the invention, or an illumination system according to the invention, preferably having an illumination profile, particularly of the homogeneity of the intensity of the lateral emission in the operating state, adapted to the application purpose.

A method is provided for producing a diffuser base body according to the invention, in particular for an illumination system according to the invention, comprising at least one scattering element, the at least one scattering element preferably being aligned along the longitudinal axis of a diffuser base body substantially parallel thereto or being arranged at an angle with respect to the longitudinal axis of the diffuser base body, containing the method steps: providing a multiplicity of light guide rods consisting of a glass having the refractive index $n_1$ and/or $n_1'$, arranging the multiplicity of light guide rods having the refractive index $n_1$ and/or $n_1'$ and at least one scattering rod consisting of a glass or a glass ceramic, which comprises scattering centers, so that the longitudinal axes of the light guide rods and of the at least one scattering rod extend substantially parallel to one another and a preform is obtained, heating the preform, drawing the preform in drawing equipment and optionally cutting to length, in order to obtain a diffuser base body.

In the diffuser base body obtained in this way, the outer circumferential faces of the light guide rods are connected inseparably, with a form fit to one another and to the at least one scattering rod. In particular, they are fused to one another and therefore form the matrix of the diffuser base body having at least one scattering element which is incorporated and/or adjacent thereto, formed from the at least one drawn scattering rod.

A multiplicity of light guide rods consisting of a glass having the refractive index $n_1$ or $n_1'$ are therefore provided.

Depending on the illumination profile to be achieved, at least one or a plurality of scattering rods consisting of a glass or glass ceramic, containing the described scattering centers, are provided in a required number and are arranged next to or between the light guide rods, so that an arrangement of light guide rods and scattering rods is obtained in which the longitudinal axes of light guide rods and scattering rods are advantageously arranged substantially parallel to one another. The distribution of the scattering rods in the arrangement may be carried out according to a pattern dependent on the desired illumination profile. This arrangement is fixed by suitable means and thus forms a preform.

In a subsequent method step, the preform is heated and drawn to form a laterally emitting glass element, so that the light guide rods and the at least one scattering rod connect inseparably to one another on their outer circumferential faces. The temperature management during the drawing also leads to a phase boundary remaining between the light guide elements. This may, in particular, be achieved by the drawing temperature being kept below the melting temperature of the glass of the light guide rods and the latter in particular being sintered together at the sintering temperature. According to the invention, complete melting of the light guide rods is avoided. Likewise by the temperature management, the preferred form fit of the light guide rods and if required also of the scattering elements is achieved.

The glass element obtained in this way may directly form the diffuser base body. In particular, however, the diffuser base body and/or sections thereof may also be obtained by finishing, for example cutting to length, the glass element which has been produced. The matrix of the diffuser base body is in this case formed from the drawn light guide rods connected with a form fit, in which the at least one scattering element having the scattering centers, which is formed from the drawn scattering rods, is incorporated likewise with a form fit, substantially according to its arrangement in the preform.

In one advantageous embodiment, the light guide rods are not entirely fused to one another as described, and the scattering rod is also not entirely fused to at least one of the light guide rods. A phase boundary may then also be present between the scattering rod and the light guide rods, and therefore also remains inside the matrix which is formed and the scattering elements of the diffuser base body. This embodiment may be achieved by the softening temperature of the glass of the light guide rods being equal to or less than the softening temperature of the scattering rods.

One likewise advantageous embodiment provides that the light guide rods are not entirely fused to one another and there is a phase boundary between them, but the at least one scattering element is fused onto at least one light guide rod. This may be achieved by the softening temperature of the glass of the scattering rods being selected to be less than that of the glass of the light guide rods. A softening temperature of the glass of the scattering rods which is up to 50 K lower, in particular a softening temperature which is up to 30 K lower, has proven advantageous.

During the drawing, the matrix is formed from the light guide rods and the scattering elements of the glass element are formed from the scattering rods. The light guide rods therefore consist of a glass having a refractive index $n_1$ and are specifically not encapsulated by a cladding glass having the refractive index $n_2$.

The means for fixing the arrangement of the preform consisting of light guide rods and scattering rods may for example be clamps, which are subsequently removed again.

The matrix obtained in this way, having the at least one scattering element, is provided with the solid encapsulation in a further drawing process. In the context of the invention, a solid encapsulation is preferably used, which may be formed with a multipart or multilayer structure. In a preferred embodiment, this solid encapsulation comprises at least two, particularly preferably at least three encapsulating tubes.

In order to produce a solid encapsulation having two encapsulating tubes, the matrix having the at least one scattering element may be arranged in the interior of the first encapsulating tube. The first encapsulating tube may then be placed in the second encapsulating tube.

In detail, the method may comprise the following steps: providing a matrix having the at least one scattering element, obtaining an arrangement in which the matrix having the at least one scattering element is arranged in the interior of the first encapsulating tube, placing the first encapsulating tube in a second encapsulating tube, drawing the arrangement in drawing equipment and optionally cutting to length, in order to obtain a diffuser base body having solid encapsulation.

In addition, when the assembly is drawn out in a drawing machine, the preform can be rotated about the longitudinal axis of the preform to produce, for example, a helical arrangement of the scattering centers about the longitudinal axis.

In order to produce a solid encapsulation having three encapsulating tubes, the matrix having the at least one scattering element may be arranged in the interior of the first encapsulating tube. The first encapsulating tube may then be placed in the second encapsulating tube, and this may in turn be placed in the third encapsulating tube.

In detail, the method may therefore also comprise the following step: placing the second encapsulating tube in a third encapsulating tube before the arrangement is drawn in drawing equipment.

The order of the assembly may of course also be configured differently, so long as light guide rods and scattering rods, first, second or even third encapsulating tubes are correspondingly preassembled. This arrangement may then be delivered to a drawing process in drawing equipment, in order to fuse these components to one another to form a compact, continuous body which may represent the basis for the desired diffuser element.

At least one of the encapsulating tubes may in this case be sealed on one side, which makes assembly and obtaining the arrangement easier.

Surprisingly, such preassembled arrangements with three encapsulating tubes or even more encapsulating tubes as well as a matrix having at least one scattering element in the interior may also be shaped as a whole in one drawing process in a single step to form the desired diffuser element. During the heating and drawing, the encapsulating tubes soften and press onto the component respectively arranged further inside, so that a triple cladding is essentially formed around the matrix having the scattering element.

The product obtained by the heating and drawing may subsequently be divided or cut to length and/or correspondingly processed further.

By varying the parameters: speed, temperature and/or force in the drawing process, optionally after finishing, tapering diffuser base bodies that are conical at least partially or in sections may be obtained. At least in the region of a taper, the scattering elements then extent no longer parallel to the longitudinal axis of the diffuser base body but at an angle with respect thereto.

A preferred application of the illumination system as has been described above in its various embodiment variants provides the use for photodynamic therapy (PDT) or photoimmunotherapy (PIT), for example for tumor therapy, for endovenous laser therapy (EVLT), for example for treating varicose veins, for laser-induced interstitial thermotherapy (LITT), for example for treating epilepsy or brain tumors, or for applications in the field of dental medicine, ophthalmology and dermatology, as described in the introduction. In the field of dental medicine, in particular applications for wound or periodontitis treatment may be mentioned here. There are furthermore applications in brain research, in which individual brain regions can be stimulated by means of light and disease symptoms can therefore be treated.

A further application of the illumination system as has been described above in its various embodiment variants provides the use for photodynamic therapy (PDT) for tumor therapy, wherein at least one light guide having the diffuser element receives light emitted from other diffuser elements and forwards it through the light guide to a detector for spectroscopic analysis. In this case, besides the various light-emitting diffuser light guides, light-receiving diffuser light guides are also applied to the patient, in which case a response to the PDT treatment may be deduced with the aid of the spectral differences between the light coupled in and the received light (see in this regard Finlay et al., Proc. SPIE Int. Soc. Opt. Eng. 2014, June 14; 5315: pages 132-142). In addition, dosimetric tasks may also be carried out in this way.

Furthermore, applications in the industrial sector are also advantageous, for instance to inspect inaccessible positions for example on or in a machine, for which in particular homogeneous illumination is important, or else spectroscopic applications or applications in biochemistry, for which in vitro biochemical responses are stimulated by light.

BRIEF DESCRIPTION OF DRAWINGS

The invention will be explained in more detail below with the aid of an exemplary embodiment which is represented in the figures, in which.

DETAILED DESCRIPTION

In the following description of the detailed embodiments, references that are the same in the appended figures respectively refer to components which are the same or have the same effect.

For better understanding, the following definitions will be given.

In the context of the present disclosure, the term illumination system covers illumination apparatuses and, in particular, illumination apparatuses which are suitable for use for medical technology purposes, and which in particular can be disinfected and/or sterilized at least in sections, if they are intended to come into contact with living tissue.

The term "for a medical technology therapy and/or diagnosis system" also includes the use or application of the illumination system disclosed here itself as a medical therapy and/or diagnosis system.

Figure 1:
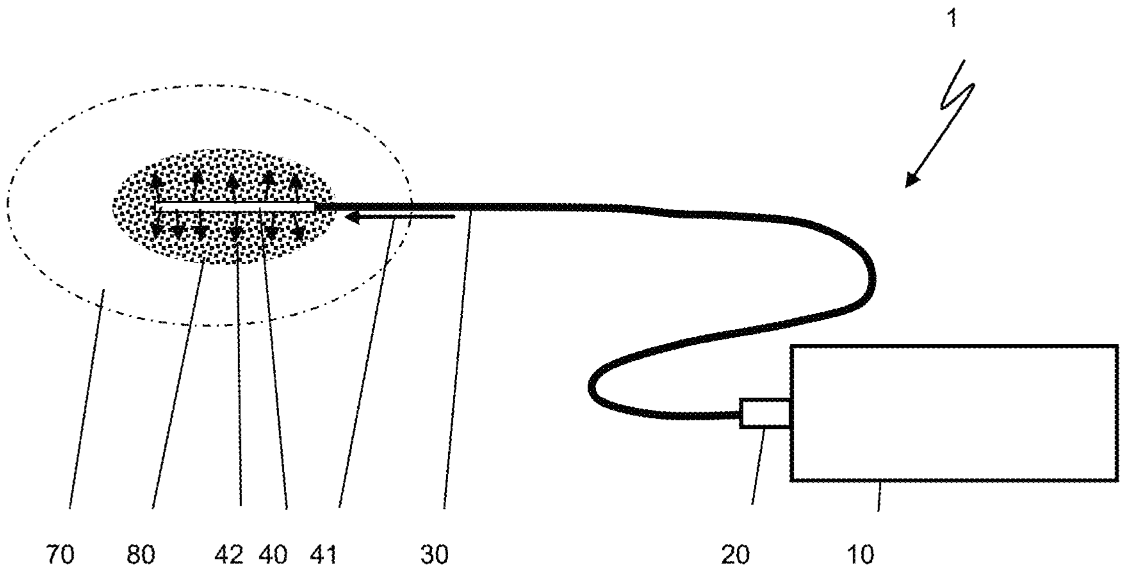
FIG. 1 schematically shows an illumination system having a light guide and a diffuser element in a PDT application.

FIG. 1 schematically shows the structure of an illumination system 1 according to the one preferred embodiment of the invention. A medical technology PDT application is represented here by way of example.

In the example shown, the illumination system 1 comprises a light source 10, in particular a laser light source, which in the operating state emits light in a particular spectral range. For PDT applications, such as are described in the introduction, lasers are used which emit a wavelength matched to the previously administered biochemically modified dye (photosensitizer), usually in the visible range, for example in the green spectral range at 532 nm or in the red spectral range, for example at 690 nm. It should be noted here that light sources based on LEDs or LDs may in principle also be used. In respect of the achievable power densities, however, laser-based systems have gained predominance.

A light guide 30 is connected by a jack 20 at its proximal end to the light source 10. Here, the proximal end refers to the end of the light guide 30 into which light is coupled. At the distal end, the light guide 30 has a diffuser element 40, which can be introduced by means of cannulas (not represented here) into a tumor tissue 80 which has been formed inside a healthy tissue 70. The region of effect of the diffuser element corresponds in the ideal case to the region of the tumor tissue 80.

The distal end in this case refers to the other end of the light guide 30, which is generally arranged at a distance from the proximal end of the light guide 30 and from which, in particular, light emerges.

The laser radiation in this case passes through a light input 41 on the diffuser element 40 into the diffuser element 40 and is laterally emitted over the length of the diffuser (light output 42). In this case, maximally homogeneous emission over the length of the diffuser element 40 is important. In particular, intensity peaks are to be avoided. By a photoinduced biochemical response, as described in the introduction, death of the tumor tissue 80 ideally takes place after the treatment. In general, quartz fibers are used as the light guide 30, the jacks 20 generally being configured as coaxial jack connector, so-called SMA jacks, in which the fibers are adhesively bonded into the jack 20. Jacks 20 having nickel-silver sleeves, in which the light guide 30 is introduced, crimped, into the nickel-silver sleeve with a form fit by plastic deformation, may also be advantageous in respect of the thermal load-bearing capacity. Furthermore, for relatively high laser powers, it is also possible to use jacks 20 in which the fiber end of the light guide 30 is protected by a conical prism, which may be advantageous in respect of misalignments. The light guide may, as described above, comprise a single fiber, for example a single-mode or multimode light guide fiber, comprising a core having a core diameter and a cladding, or a fiber bundle having a fiber bundle diameter.

Figure 2:
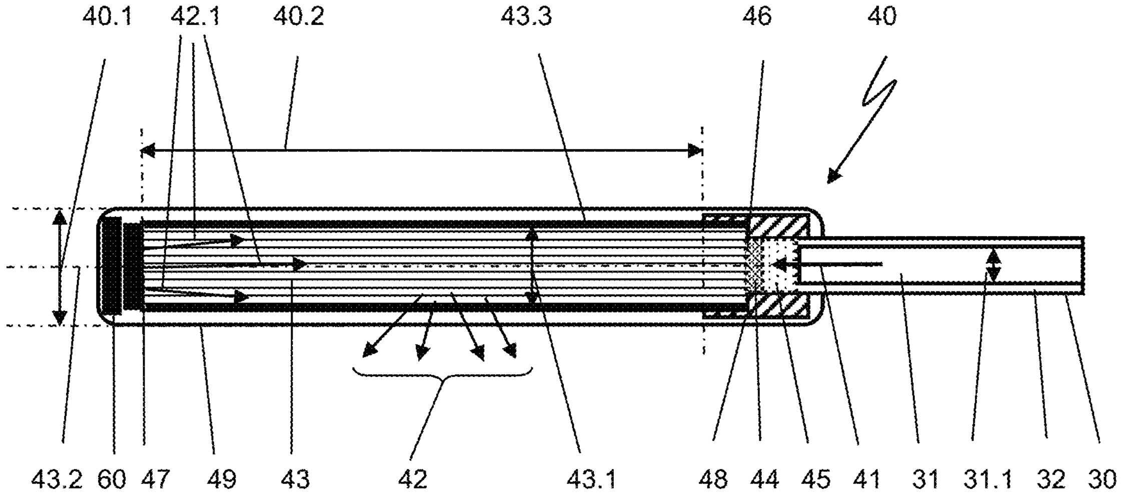
FIG. 2 shows the diffuser element in a schematic longitudinal-sectional representation.

FIG. 2 schematically shows the structure of a diffuser element 40 according to a preferred embodiment of the invention.

The diffuser element 40 consists of a diffuser base body 43, which is fastened by means of a connecting zone 44 to the light guide 30. In the applications described above, the light guide 30 usually consists of quartz glass having a core 31 with a refractive index $n_1$ and a core diameter 31.1 of usually between 200 and 600 μm, as well as a cladding 32 with a refractive index $n_2$, where $n_1>n_2$. The numerical aperture NA usually achievable by means of this is about 0.22. The light input 41 takes place through an coupling area 46 of the diffuser base body 43. The light guide 30 usually also has an outer cladding 33, usually consisting of a polymer, for example PMMA, PA (for example NYLON®) or a fluorinated polymer (for example TEFZEL®, which is also referred to as a buffer. This is not represented in FIG. 2.

The diffuser base body 43 with its diameter 43.1 comprises, in a preferred embodiment, a solid encapsulation 43.3 and a matrix 43.4 of matrix elements 43.5 with incorporated scattering elements 43.6 or consists of a solid encapsulation 43.3 and a matrix 43.4 of matrix elements 43.5 with incorporated scattering elements 43.6.

Purely by way of example, FIGS. 6a, 6b, 6c and 6d represent various exemplary embodiments of favorable arrangements of scattering elements 43.6 in a diffuser base body 43. Furthermore, FIGS. 7a and 7b represent various exemplary embodiments of scattering elements in a matrix 43.4 of the diffuser base body 43. These exemplary embodiments will be discussed in more detail further below.

According to the invention, the solid encapsulation 43.3 may consist of or comprise a plurality of, preferably at least two, encapsulating tubes or layers 43.3.1, 43.3.2, 43.3.3, which are arranged coaxially with respect to one another and may have different optical properties in respect of at least the transparency, the refractive index and/or the material of the encapsulating tube.

In order to be able to satisfy the homogeneity requirements in respect of the intensity of the lateral emission in the operating state, the diffuser base body 43 comprises between 10 and 100 scattering elements 43.6, depending on the operating wavelength and the diffuser length. As a rule of thumb: the longer the application wavelength or the shorter the diffusion length, the more scattering elements 43.6 are to be provided.

The ratio of the cross-sectional areas of incorporated scattering elements 43.6 and the diffuser base body 43 is given as ≤0.015, preferably ≤0.005, particularly preferably ≤0.002. The scattering elements 43.6 are in this case aligned substantially parallel to the longitudinal axis 43.2 over the entire length of the diffuser base body 43.

In one advantageous configuration, the diameter of the diffuser base body 43 is configured to be greater than the core diameter 31.1 or fiber bundle diameter 31.1 of the light guide 30, so that on the one hand no uncontrolled scattered light is for example coupled into the solid encapsulation 43.3. On the other hand, assembly and the adjustment of the light guide 30 and the diffuser base body 43 can therefore be facilitated and/or assembly tolerances can be compensated for. The ratio of the core diameter 31.1 or fiber bundle diameter 31.1 of the light guide 30 and the diameter of the diffuser base body 43.1 with the incorporated scattering elements 43.6 is therefore advantageously ≤1.0, preferably between 1.0 and 0.8. Depending on the desired emission characteristic, a ratio of ≤0.8 may also be provided.

An optical element, which may for example be configured as a beam shaping element, light guide element or fiber-optic taper, optionally conically, may be arranged in the connecting zone 44 between the proximal end of the diffuser base body 43 and the distal end of the light guide 30. Geometrical matching, for example of diameter differences, is thus also made possible. In this case, the proximal end of the diffuser base body 43 refers to the end of the diffuser base body 43 into which light is coupled.

In order to avoid scattered light from the connecting zone 44 but also as mechanical stabilization of the connecting zone 44, according to one preferred embodiment of the invention, a sleeve 48 consisting of plastic, glass, metal or ceramic material through which light from the light guide 30 can pass in the direction of the longitudinal axis of the light guide 30 and can pass at particular lateral angles, but by which light that may enter at the extremity into the proximal end of the scattering body is blocked, is provided. A sleeve 48 consisting of a borosilicate-like glass has proven particularly effective in respect of avoiding light absorptions. Such a glass is known, for example, under the designation SCHOTT FIOLAX® 8412 from the manufacturer Schott AG.

At the distal end of the diffuser base body 43, opposite to the proximal end, in order to optimize the emission characteristic a reflector face 47 is provided, which may be configured to be directionally reflective as a mirror element in the form of a metal sheet or as a thin mirror film, for example a carrier film with a vapor-deposited mirror layer or a coating having a reflectivity >95%. A diffusely reflective layer has also been found to be advantageous, for example by means of application, for example printing, with a preferably white color.

In another configuration variant, it can be provided that the reflector face 47 is produced as short, polished wire sections consisting of aluminum or gold, which are brought directly into contact with the diffuser base body 43. This also provides small heat sinks which help to avoid hotspots.

Furthermore, sputtered or vapor-deposited dielectric reflection layers on the distal end of the diffuser base body 43, which consist of a plurality of layers and are matched in respect of reflectivity to the wavelength of the light used, have been found to be particularly advantageous. Geometrical embodiments of reflector faces 47 will be described further below. In this way, for example, it is possible to achieve a reflectivity of >95%, preferably >99%.

The term "matched in respect of reflectivity to the wavelength of the light used" in the scope of the present invention indicates that, with the matching, a maximally high reflectivity is achieved at this wavelength or even the maximum of the reflectivity lies at the wavelength to which matching is respectively carried out. An example of such a reflector layer is a multiple layer system consisting of alternately applied $TiO_2$ and $SiO_2$ layers, which for example has a reflectivity of >99%, preferably >99.5%, in the application wavelength range, for example for red light at (690±10) nm.

Such layer systems may correspondingly be adapted to the respective application wavelength, that is to say matched as indicated above. In this way, it is possible to achieve ideal back-reflection on the one hand and avoidance of hotspots on the other hand. As an alternative thereto or in addition, silver layers with rear-side passivation may also be provided as a reflector face 47. Protection of the reflector layer at the distal end, for example by means of a drop of adhesive, which then forms a rounded cap in the cured state, is likewise conceivable.

Since a so-called pilot light for setting up, i.e. for positioning the diffuser for example in vivo, is often used in a PDT or PIT application, and this differs significantly in respect of the power and above all the wavelength from the application wavelength (for example 690 nm), on the one hand an additional blocking element 60, for example in the form of a ceramic or metal cylinder, a ceramic or metal sphere, may be provided behind the reflector face 47 as seen in the distal direction, and/or the layer system of the reflector face 47 is configured in such a way that a high reflectivity of >80%, preferably >95%, particularly preferably >99% for the wavelength of the pilot light, for example in the green spectral range between 500 nm and 580 nm, can additionally also be achieved.

Metallic blocking elements 60 furthermore have the advantage that they can be identified as so-called radio-markers or x-ray markers in the X-ray image. This also applies for the sleeve 48 or an additional sleeve in the region of the connecting zone 44, if the latter is configured as a thin-walled metal sleeve. Typically, such metal sleeves are made of a material or materials, a combination or alloy thereof, with a high atomic number. Examples include tantalum, platinum, iridium, or platinum-iridium alloys.

For further mechanical protection and/or for homogenization of the emission characteristic, an encapsulation 49 consisting of transparent and/or translucent, colored or colorless material (silicone, glass or quartz glass) may be provided, which encloses the diffuser base body at least partially or in sections. In particular, with a material which is translucent and/or contains scattering centers, additional homogenization may be achieved. For example, corresponding bodies or tubings consisting of silicone, polytetrafluoroethylene or else of a poly(ether-block-amide) block copolymer, which is for example known in the market as PEBAX®, are suitable. Thin-walled shrink tubings, for example consisting of PET, which may be configured in one layer or multiple layers, applied at least in sections have proven suitable as an encapsulation 49. The light output 42 according to a Lambertian emitter is thus further reinforced or implemented. An active length 40.2 of the diffuser element 40 is then given as the distance between the sleeve 48 and the reflector face 47, and may for example extend over up to the entire length of the diffuser element 40 or over an active length 40.2 of the diffuser element 40.

Between the diffuser base body 43 and the encapsulation 49 consisting for example of glass or plastic, it can be provided that an immersion layer is introduced between the encapsulation 49 and the diffuser base body 43 in order to suppress any surface irregularities, for example contamination, roughness or the like, on the diffuser base body 43, which unfavourably influence the emission behavior. In this case, it is necessary to ensure on the one hand a refractive index matched to the glass system, a high transparency and a sufficiently high viscosity in respect of good applicability. For example, glycerin or silicones (oils or adhesives) have been found to be suitable as an immersion layer.

In order to avoid perturbing reflections, it can be additionally provided that the reflector face 47 is covered with or formed by an encapsulation or cap 47.2 laterally encompassing the diffuser base body 43 on its circumferential face on a short length. In this case, the active length 40.2 corresponds to the distance between the sleeve 48 and this protective cap. If the sleeve 48 and the cap 47.2 are made of metal, a radio-marker function may therefore be achieved, which makes the active length 40.2 or the position of the diffuser element 40 identifiable in the X-ray image. The overall diameter 40.1 of the diffuser element 40 is typically between 0.8 and 1.2 mm for PDT applications. Diameters 40.1 of just under 1 mm are usual. What is crucial here is the diameter of the cannula through which the diffuser elements 40 are applied to the patient.

The fastening of the diffuser base body 43 and the light guide 30 is carried out inside the connecting zone 44 by, for example, a splicing or adhesive bonding process with a highly transparent, refractive power-matched adhesive. During the splicing, the light guide 30 and the diffuser base body 43 are partially fused, or fused, by means of a corona discharge and/or by means of a laser, usually with a $CO_2$ laser, and joined together. Depending on the material which is used for the diffuser base body 43 and the light guide 30, it may be necessary for an intermediate medium 45 to be used in order to match their thermal expansion coefficients. In the case of glass/quartz fusion, this may for example be a solder glass or junction glass or an optical adhesive or cement. Mechanical pressing in the form of a bushing is also conceivable and advantageous to implement, the transition merely being filled with an optical cement in order to avoid reflection losses. An optical element arranged in the connecting zone 44 between the proximal end of the diffuser base body 43 and the distal end of the light guide 30 may likewise be incorporated or connected.

The diffuser base body 43 comprises a matrix 43.4 in which the scattering elements 43.6 are embedded in a preferred arrangement parallel to the longitudinal axis 43.2, as also shown in the embodiment of FIG. 2, over the entire length of the diffuser base body 43. The axial extent of individual scattering elements may in this case be less than the overall length of the diffuser base body 43. In this case, the scattering elements 43.6 may be arranged distributed more or less statistically uniformly over the diameter 43.1 of the diffuser base body 43, that is to say a multiplicity of scattering elements 43.6 which are arranged around the longitudinal axis are present; preferably, the scattering elements are arranged in a regular structure around the longitudinal axis.

In one exemplary embodiment, the diffuser base body 43 respectively has a solid encapsulation 43.3 and a matrix 43.4, in which the scattering elements 43.6 are embedded in a preferred arrangement parallel to the longitudinal axis 43.2 over the entire length of the diffuser base body 43.

Figure 6A:
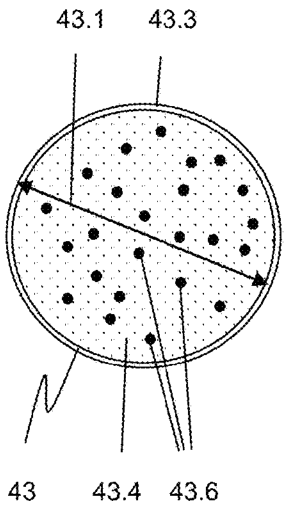
FIG. 6*a*, 6*b*, 6*c*, 6*d* show various exemplary embodiments of the arrangement of scattering elements in a diffuser base body.
Figure 7A:
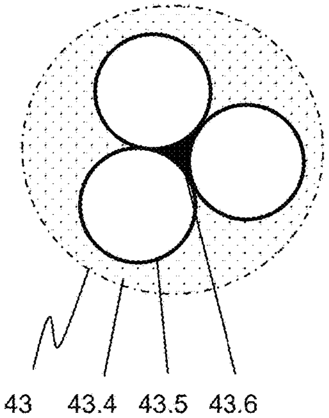
FIGS. 7*a* and 7*b* show various exemplary embodiments of scattering elements in a matrix of the diffuser base body, FIGS. 8a, 8b and 8c schematically show various configuration examples of a reflector face of the diffuser base body, and FIG. 9 a schematic drawing of a diffuser base body with a helical arrangement of the diffusion centers around the longitudinal axis of the diffuser base body.
Figure 7B:
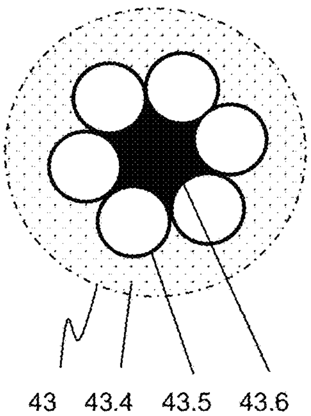

FIG. 6*a* shows an arrangement in which a multiplicity of scattering elements 43.6 are arranged distributed more or less statistically uniformly over the diameter 43.1 of the diffuser base body 43, that is to say a multiplicity of scattering elements 43.6 which are arranged around the longitudinal axis are present; preferably, the scattering elements are arranged in a regular structure around the longitudinal axis.

Figure 6B:
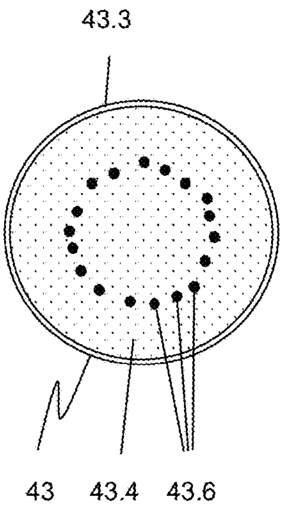
Figure 6C:
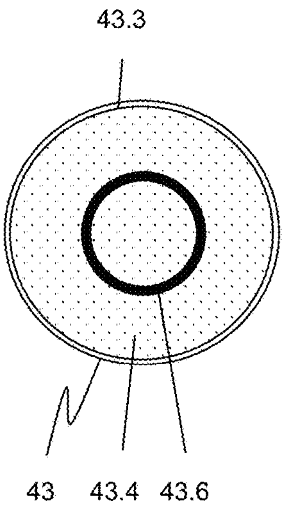
Figure 6D:
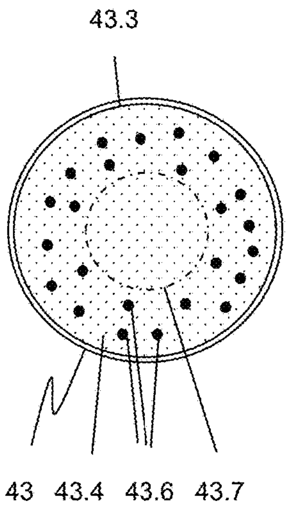

FIG. 6*b* shows an arrangement in which individual scattering elements 43.6 form an in particular annular arrangement, that is to say a multiplicity of scattering elements which are arranged around the longitudinal axis, preferably circularly are present.

In another exemplary embodiment, only one scattering element 43.6 in the form of a tube or tube section is embedded in the matrix 43.4, that is to say the at least one scattering element (43.6) is arranged tubularly around and in particular coaxially with respect to the longitudinal axis. An advantage of this arrangement is particularly economical and reproducible production of the preform of the diffuser base body 43, since the production process can be simplified considerably here.

In principle, other geometries are also conceivable and advantageously implementable for the at least one scattering element 43.6 and/or the arrangement of a multiplicity of scattering elements 43.6, for example hexagonal, square, triangular.

As an alternative, it can be provided that the scattering elements 43.6 are arranged more or less equidistributed in the matrix 43.4, although they leave a core zone 43.7 around the longitudinal axis 43.2 of the diffuser base body 43 free, that is to say the number of scattering elements 43.6 per unit area of the cross-sectional area of the diffuser base body 43 outside a core zone 43.7 along the longitudinal axis is greater than that of per unit area in the core zone 43.7.

This arrangement has the advantage that the laser light, which typically has only a small numerical aperture (NA, typically <0.3), after coupling into the diffuser base body 43, is initially scattered less at the scattering elements 43.6 in the outer region around the core zone 43.7, and is scattered more greatly only after some distance from the input face 46, when the individual rays reach the scattering elements 43.6 in the edge region. It is therefore possible to achieve an intensity reduction of the laterally emitted light directly after the input face 46, and therefore homogenization of the intensity profile along the diffuser.

With a constant concentration of scattering elements along the longitudinal axis of the diffuser base body, the intensity profile has a typically exponential decrease with $I(l)=I_0 \times e^{-l/k}$. In this case, it has found to be a favorable value for k if k corresponds approximately to the length of the diffuser base body (in the specific example 40 mm). This approximately gives a 1/e decrease of the laterally emitted intensity of the radiation in the operating state along the diffuser base body, which may be corrected by the further measures in such a way that the aforementioned homogeneity requirements can be satisfied, in particular for PDT applications. In a preferred exemplary embodiment, with 21 scattering elements each having a diameter of 0.3 mm as starting material for the preform and a matrix diameter of about 600 μm (starting geometry with a preform having a diameter of 34 mm), a k value of 42 mm was determined.

In one particularly preferred embodiment of the invention, the diffuser base body 43 furthermore comprises a solid encapsulation 43.3 which encloses the matrix 43.4 at least in sections on the cladding face. In the exemplary embodiment depicted in FIG. 2, the cladding face of the matrix 43.4 is fully enclosed by the solid encapsulation 43.3, although enclosure at least in sections may also be sufficient.

The solid encapsulation 43.3 is advantageously configured with a multipart or multilayer structure comprising at least two encapsulating tubes or layers, preferably at least three encapsulating tubes (43.3.1, 43.3.2, 43.3.3) and/or layers.

In order to homogenize the intensity profile, but also particularly in order to prevent undesired return of the light into the delivery fiber, which may in particular compromise the stability of a light source 10 configured as a laser light source, to the extent of perturbations in its regulation or even the laser light source being turned off, or may lead to undesired heating of the jack connection, according to the invention further measures for widening the numerical aperture NA of the light 42.1 reflected back at the reflector face 47 are conceivable.

This may advantageously be carried out by at least in regions grinding the distal end face, or the reflector face 47, at an angle not equal to 90° with respect to the longitudinal axis 43.2 of the diffuser base body 43.

Figure 8A:
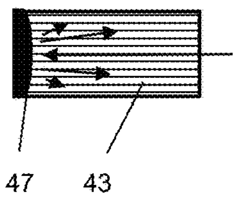
Figure 8B:
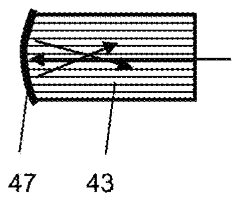

Further embodiments of the reflector face 47 are schematically shown by FIGS. 8*a* and 8*b*. Accordingly, in order to homogenize the intensity profile, it can be provided that the reflector face 47 is configured to be concave (FIG. 8*a*) or convex (FIG. 8*b*). In this way, it is possible to achieve the effect that reflected rays having an almost parallel profile with respect to the longitudinal axis 43.2 are reflected back at a steeper angle with respect to the longitudinal axis 43.2 and are therefore scattered more frequently at the scattering elements 43.6, so that the output efficiency at the distal end of the diffuser element 40 is increased.

In addition, a radiation component which is reflected back particularly into the light guide 30 can therefore be substantially reduced. Further measures, which in particular may also be carried out economically, may be grinding of the diffuser base body 43 at an angle not equal to 90° with respect to the longitudinal axis 43.2. Facet-like grinding, in which the individual faces make different angles, predominantly in each case not equal to 90°, with respect to the longitudinal axis 43.2 of the diffuser base body 43, may likewise be effective. The angular deviation from 90° is usually less than 5°.

Figure 8C:
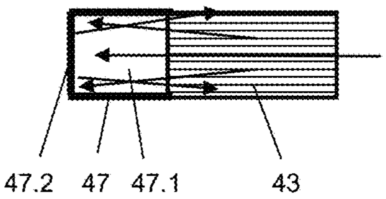

The reflector face 47 at the distal end of the diffuser base body 43 may also be configured as a hollow and/or transparent body 47.1 having an encapsulation 47.2 reflecting into the cavity and/or into the transparent body, as is schematically shown in FIG. 8*c*. The encapsulation 47.2 may be configured as a preferably directionally or diffusely reflective coating and/or cap. These may also terminate without a cavity directly with the diffuser base body 43 and radially contain the latter in both cases over a short length at the distal end at least partially or in sections on its circumference.

Accordingly, the reflector face 47 may be configured concavely or convexly, and/or as a body 47.1 and/or encapsulation 47.2 forming a cavity directly or at a distance between the reflector face 47 and the distal end of the diffuser base body 43, following on from the diffuser base body 43 as a hollow body closed on one side.

Figure 9:
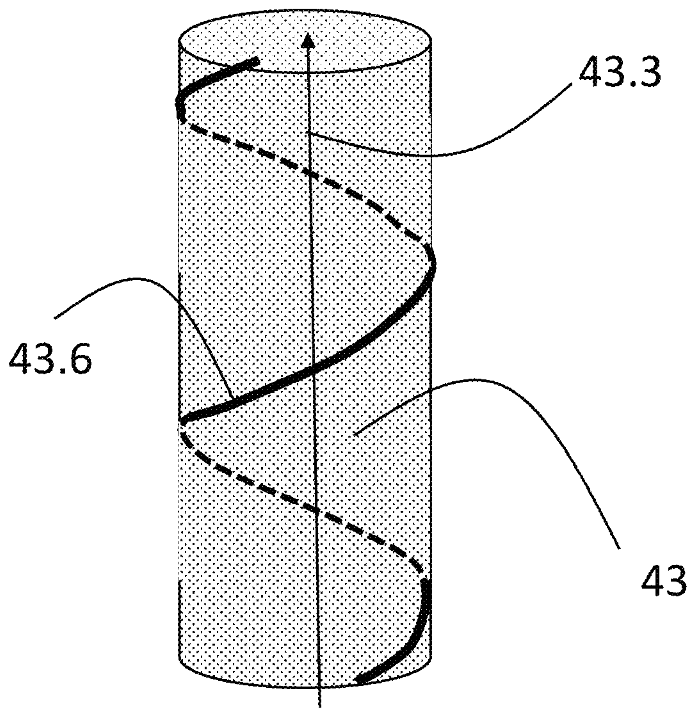

FIG. 9 schematically shows an example of only one filament-like scattering element 43.6 of the diffuser base body 43 in a helical arrangement about the longitudinal axis 43.2 of the diffuser base body 43. Such a helical structure can be obtained if, in addition, the preform is twisted about the longitudinal axis of the preform when the arrangement is drawn out in a drawing machine, thereby producing this helical arrangement of the scattering centers 43.6 about the longitudinal axis 43.2.

Figure 3:
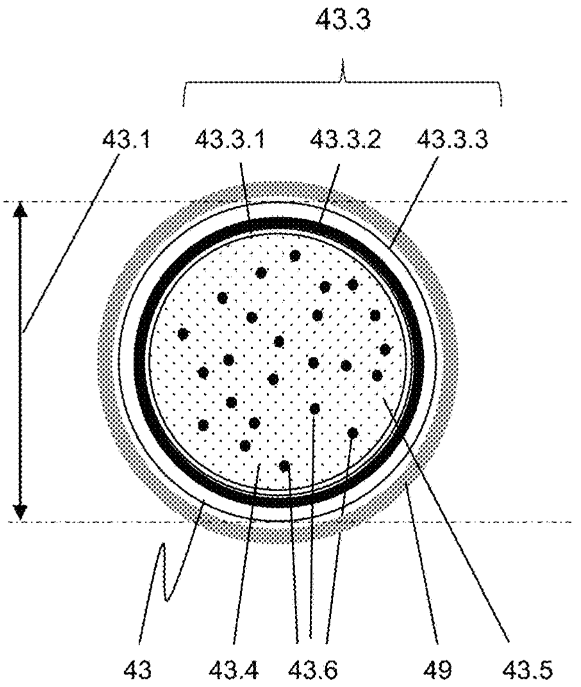
FIG. 3 shows a preferred exemplary embodiment of the arrangement of scattering elements in a diffuser base body in a schematic cross-sectional representation.

FIG. 3 shows a schematically represented cross section of a diffuser base body 43 according to the invention with its diameter 43.1 and a solid encapsulation 43.3 enclosing the matrix 43.4, in which this solid encapsulation 43.3 enclosing the matrix 43.4 with the scattering elements 43.6 is constructed from a plurality of coaxial encapsulating tubes 43.3.1, 43.3.2, 43.3.3, which have different optical properties. The matrix 43.4 is in this case constructed from individual matrix elements 43.5.

In the context of the invention, however, embodiments having two encapsulating tubes 43.3.1, 43.3.2 arranged coaxially with respect to one another are also possible and conceivable.

According to the particularly preferred exemplary embodiment of the invention depicted in FIG. 3, the first encapsulating tube 43.3.1, which encloses the matrix 43.4, consists of a transparent material, the refractive index being lower than the refractive index of the matrix 43.4. This is also referred to as optical cladding, and ensures that the light coupled in according to the light input 41 can be initially guided in the matrix 43.4 and can therefore interact with the scattering elements 43.6, so that a high scattering efficiency can already be achieved here.

The second encapsulating tube 43.3.2 is configured in the exemplary embodiment as a scattering, i.e. translucent tube in which further scattering elements are incorporated. In this way, in particular so-called cladding modes which are coupled at the reflector face 47 back into the cladding, or into the first encapsulating tube 43.3.1, can be output from the diffuser base body 43, which additionally reinforces the emission intensity of the emission 42. The second cladding tube 43.3.2 can also be designed as an annular arrangement of individual highly scattering white glass rods.

In this case, the second scattering encapsulating tube 43.3.2 must be optically coupled to the first encapsulating tube 43.3.1 and the refractive index of the second encapsulating tube 43.3.2 must be higher than the refractive index of the first encapsulating tube 43.3.1. In this way, almost isotropic emission can be achieved because of the multiple scattering in the second encapsulating tube 43.3.2. Furthermore, additional homogenization is achieved in this way.

The third, outer encapsulating tube 43.3.3 is used as mechanical stabilization in particular for the second encapsulating tube 43.3.2, and therefore makes it possible to form a compact and robust diffuser base body 43 by the drawing process. In addition, as already described above with reference to FIG. 2, an encapsulation 49 consisting of a thin-walled polymer material which can be configured to be clearly transparent, slightly translucent and/or also color-doped, may enclose the diffuser base body 43 and a part of the light guide 30.

In a preferred embodiment, the matrix 43.4 consists of an optically highly transparent glass, such as is constituted by the optical glass SCHOTT N BK-7 from the company Schott AG, for example. The scattering elements 43.6 may, for example, consist of a white glass.

As the first encapsulating tube 43.3.1 and as the third encapsulating tube 43.3.3, a highly transparent borosilicate-containing glass with the designation SCHOTT FIOLAX® 8412 from the company Schott AG has proven particularly suitable. This has a transmission of about 92% in a wavelength range of wavelength from 250 to 2000 nm, and is therefore considered to be highly transparent in the context of the invention.

The second encapsulating tube 43.3.2 consists, in a preferred embodiment, of a white glass tube and may in this case be constructed similarly or identically as is the case for the scattering elements 43.6 in the matrix 43.4, if white glass is used for this purpose.

This structure has the advantage that all these components can be fused to one another very well and therefore make it possible to form a compact diffuser base body 43 which does not contain any cavities, for example in the form of air gaps or air bubbles.

Typical layer thicknesses for the encapsulating tubes 43.3.1, 43.3.2, 43.3.3 are, for a diameter 43.1 of the diffuser base body 43 of 500 μm, in a range of from 5 μm to 50 μm, preferably from 7 to 40 μm, particularly preferably about 10 μm to 30 μm, or 10 μm.

Other constructions of the solid encapsulation 43 are possible and conceivable. Thus, the solid encapsulation 43 may of course also be constructed from a combination of encapsulating tubes and/or layers, or for example more than three encapsulating tubes or layers, if further functionalization is desired. It is therefore also possible to provide further encapsulating tubes, which then enclose the third encapsulating tube at least in sections.

Constructions having only a first encapsulating tube 43.3.1 and a second scattering encapsulating tube 43.3.2 are also conceivable. In an embodiment of the invention having only two encapsulating tubes 43.3.1, 43.3.2, the first encapsulating tube 43.3.1 may be highly transparent and the second encapsulating tube 43.3.2 may be configured as a white glass tube, as explained above. In this case, the second encapsulating tube 43.3.2 may also already ensure the mechanical stabilization.

FIGS. 7*a* and 7*b* schematically show two further exemplary embodiments of the structure of the matrix 43.4 in the diffuser base body 43 in a cross section perpendicular to the longitudinal axis of the diffuser base body 43.

FIG. 7*a* shows by way of example a scattering element 43.6 which is incorporated in the preform as a thin bar between the matrix elements 43.5 in the form of individual rods. In the example shown, the scattering element 43.6 fills the intermediate spaces (interstices) of three individual rods as matrix elements 43.5. In the example shown, individual glass rods having a diameter of 2 mm were used as matrix elements 43.5 for the production of the preform. The scattering elements are formed from 0.3 mm thick white glass rods. After the thermal drawing process, that is to say after drawing down to the diameter 43.1 of the diffuser base body 43, the scattering element 43.6 is partially fused, or fused, and has a triangular, for example in particular hyperbolically triangular cross section.

FIG. 7*b* shows an alternative arrangement, in which the diameters of the scattering elements 43.6 are equal to or less than the diameters of the matrix elements 43.5 configured as individual rods. Here, the typical diameters before the drawing process in the correspondingly assembled preform lie in the range of from 0.5 to 1 mm for the scattering elements 43.6 as for example white glass bars and the matrix elements 43.5. After the thermal drawing process, that is to say after drawing down to the diameter 43.1 of the diffuser base body 43, the scattering element 43.6 is partially fused, or fused, and has a hexagonal, for example in particular hyperbolically hexagonal cross section.

The arrangement of the scattering rods in the interstices of the preform in this case makes it possible to achieve a greater number of scattering bodies, and therefore a better homogeneity, for a given size of the light guide rods and a given cross-sectional fraction. The matrix elements 43.5 and the scattering elements 43.6 may have a round, hexagonal, square or triangular cross section, in particular hyperbolic variants thereof, after the drawing process as diffuser base body 43.

The scattering elements 43.6 incorporated in the diffuser base body 43, which are incorporated in the preform as thin bars between the matrix elements 43.5 of the matrix 43.4 in the form of individual rods, fill the intermediate spaces (interstices) of three individual rods as matrix elements 43.5. Typically, individual glass rods having a diameter of 2 mm are used as matrix elements 43.5 for the production of the preform. The scattering elements are formed from 0.3 mm thick white glass rods. After the thermal drawing process, that is to say after drawing down to the diameter 43.1 of the diffuser base body 43, the scattering element 43.6 is partially fused, or fused, and has a triangular, for example in particular hyperbolically triangular cross section. Alternative arrangements are also conceivable, in which the diameters of the scattering elements 43.6 are equal to or less than the diameters of the matrix elements 43.5 configured as individual rods. Here, the typical diameters before the drawing process in the correspondingly assembled preform lie in the range of from 0.5 to 1 mm for the scattering elements 43.6 as for example white glass bars and the matrix elements 43.5. After the thermal drawing process, that is to say after drawing down to the diameter 43.1 of the diffuser base body 43, the scattering element 43.6 is partially fused, or fused, and has a hexagonal, for example in particular hyperbolically hexagonal cross section.

The arrangement of the scattering rods in the interstices of the preform makes it possible here with a given size of the light guide rods and a given cross-sectional fraction to achieve a higher number of scattering bodies and thus a better homogeneity. The matrix elements 43.5 and the scattering elements 43.6 may have a round, hexagonal, square or triangular cross section, in particular hyperbolic variants thereof, after the drawing process as diffusor base body 43.

One embodiment of the scattering elements 43.6 configured as white glass bars or of the white glass tube, or of the scattering encapsulating tube provides that scattering centers are formed by scattering particles therein, the concentrations of the scattering particles being in the scattering range of from 10 ppm to 1000 ppm and preferably from 20 ppm to 100 ppm.

The efficiency of the output from the scattering region, thus the volume of the white glass of the scattering rods or of the white glass tube, is also dependent on the concentration of the scattering particles in the scattering region itself, besides the scattering property of the scattering particles as an intrinsic parameter.

The concentration specification in ppm in this case refers to the proportion of the scattering particles in relation to the mass fractions of the constituents of the white glass in which the scattering particles are incorporated.

If inhomogeneous regions of the white glass are used as scattering centers, there is an alternative embodiment in which the inhomogeneous regions are preferably formed by phase segregation and/or demixing of the glass components of the glass in which they are incorporated.

The scattering centers formed by inhomogeneous regions preferably have a diameter of from 10 nm to 1000 nm, particularly preferably from 100 nm to 800 nm.

Particularly preferably, these scattering centers are spherical. For non-spherical scattering centers, the diameter is intended to be understood as their maximum extent.

The glass, which in the present case is referred to as white glass, in which the inhomogeneous regions are incorporated as scattering centers, may preferably consist of an As- and Pb-containing silicate glass. In this case, the scattering centers preferably have an increased Pb and/or As content compared with the surrounding glass matrix.

As an alternative, the glass, or white glass, in which the inhomogeneous regions are incorporated as scattering centers, may consist of a fluorine-containing Ca—Zn silicate glass. Then, the scattering centers preferably have an increased fluorine content compared with the surrounding glass matrix.

Figure 4:
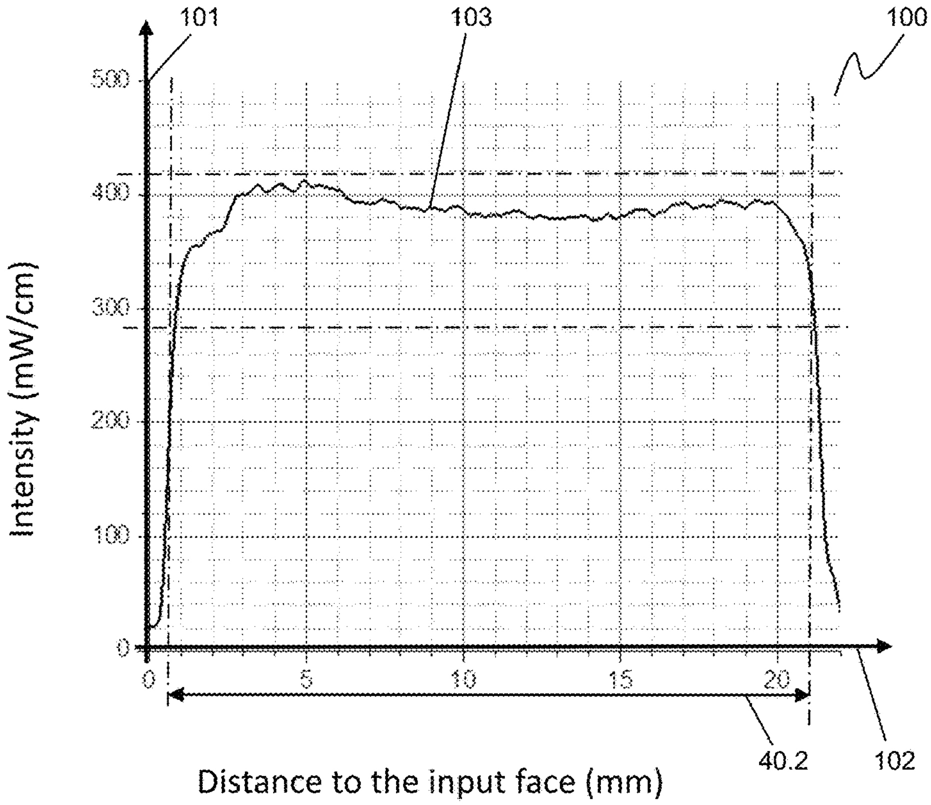
FIG. 4 shows an intensity profile in a profile diagram.

FIG. 4 represents a measured intensity profile 103 for the example of a cylindrical diffuser having an active length 40.2 of about 20 mm in a profile diagram 100. The intensity 101, here measured as "radiant exitance" in mW/cm of diffuser length is represented as a function of the distance to the coupling face 102.

The intensity profile 103 exhibits an overall relatively constant profile compared with an otherwise typically slightly exponential decrease of the intensity 101, such as is obtained as the solution of a differential equation for a scattering profile that is homogeneous over the length, that is to say there is a constant ratio of incoming radiation to scattered radiation in a length section.

By applying a reflector face 47 on the distal end of the diffuser base body 43 (cf. FIG. 2), a part of the radiation can be reflected back again, which then delivers additional scattering contributions particularly in the region before the reflector face 47. Mathematically, this means an addition of two exponential functions.

Because of the particular structure of the solid encapsulation 43.3 having at least two or even three encapsulating tubes, and the additional measures for widening the NA of the back-reflected light in order to increase the scattering efficiency, an almost homogeneous intensity profile can be achieved with deviations of <±10% from the average value over the active diffuser length 40.2. Furthermore, the overall efficiency of the desired lateral emission may be increased to >85%, typically >90%. The active diffuser length typically corresponds in this case to the length of the diffuser base body.

Figure 5:
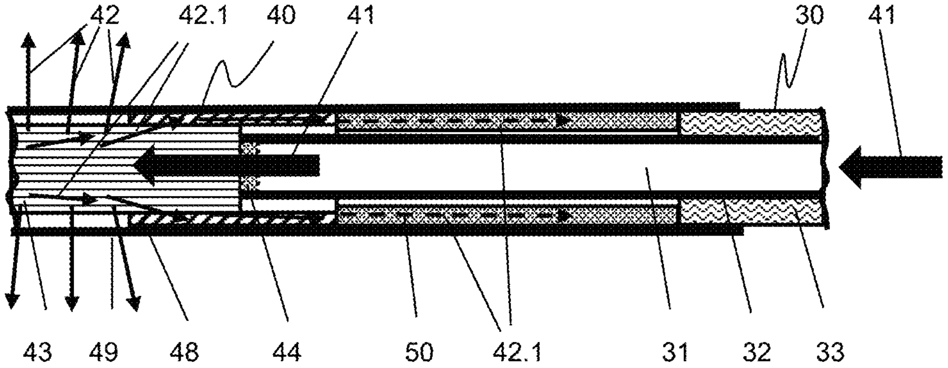
FIG. 5 shows a structure to avoid back-scattered light in the outer cladding of the light guide in a schematic representation.

FIG. 5 shows a schematic representation in sections of a structure for avoiding back-scattered light in the outer cladding of the light guide. This phenomenon may on the one hand cause illumination of the light guide 30, although this may still be regarded merely as cosmetic effect at low powers.

However, particularly at a higher laser power, for example more than 2 W, as well as a higher back-scattered light fraction, this may also result in unacceptable heating, particularly in regions where this back-reflected light impinges on components which absorb this light in a small region. Here, in particular, back-scattered light 42.1 which is guided through the transparent sleeve 48 in the direction of the laser light source, and then impinges on the outer cladding 33 of the light guide 30, has proven to be problematic. Depending on the intensity of the laser power used, or of the laser radiation, illumination of the end face of the outer cladding 33 occurs here, which may be very intense and which may then also lead to strong heating.

Assistance may be provided here by a translucent or partially absorbent encapsulation 50, which partially scatters the back-scattered light 42.1 from the sleeve and therefore significantly reduces the intensity in the region of the impingement on the outer claddings 33 of the light guide. By partial absorption and/or multiple scattering, the back-scattered light 42.1 from the partially absorbent encapsulation 50 may be minimized or distributed over a larger area, so that this back-scattered light i) is imperceptible or scarcely perceptible and ii) the power density is reduced significantly in respect of heating.

The partially absorbent encapsulation 50 according to the invention therefore ideally fills the intermediate space between the sleeve 48 and the outer cladding 33 of the light guide 30, as is schematically represented in FIG. 5. This partially absorbent encapsulation 50 may be realized as a separate element in the form of a translucent tubing section or of a shrink tubing and/or as a re-coating material, in which scattering particles are distributed. Since re-coating of the fiber in the region of the connecting zone 44, or as far as the start of the outer cladding 33, is necessary in order to maintain the level of strength, the latter may be realized in one working step. Typical re-coating materials consist of an acrylate or an epoxy material and are used for subsequent sealing of the surface of the light guide 30, which in particular increases the mechanical stability.

This measure represents a further supplement to the measures described above for avoiding an excessive back-scattered light intensity, and therefore likewise contributes to the optimization of the diffuser system according to the object.

LIST OF REFERENCES

| | |
|---|---|
| 1 | illumination system |
| 10 | light source |
| 20 | Jack |
| 30 | light guide |
| 31 | Core |
| 31.1 | core diameter or fiber bundle diameter |
| 32 | Cladding |
| 33 | outer cladding |
| 40 | diffuser element |
| 40.1 | Diameter |
| 40.2 | active length |
| 41 | light input |
| 42 | light output |
| 42.1 | back-scattered light |
| 43 | diffuser base body |
| 43.1 | Diameter |
| 43.2 | longitudinal axis |
| 43.3 | solid encapsulation |
| 43.3.1 | 1st encapsulating tube |
| 43.3.2 | 2nd encapsulating tube |
| 43.3.3 | 3rd encapsulating tube |
| 43.4 | Matrix |
| 43.5 | matrix element |
| 43.6 | scattering element |
| 43.7 | core zone |
| 43.8 | longitudinal axis of the scattering element, in particular white glass bar |
| 43.9 | white glass bar |
| 43.10 | Angle |
| 44 | connecting zone |
| 45 | intermediate medium |
| 46 | coupling face |
| 47 | reflector face |
| 47.1 | Body |
| 47.2 | reflective encapsulation/cap |
| 48 | Sleeve |
| 49 | encapsulation |
| 50 | partially absorbent encapsulation |
| 60 | blocking element |
| 70 | Tissue |
| 80 | tumor tissue |
| 100 | profile diagram |
| 101 | Intensity |
| 102 | distance to the input face |
| 103 | intensity profile |

What is claimed is:

1. An illumination system, comprising:

at least one light source;

a light guide having a light input face, at a proximal end, a distal end, and a longitudinal axis between the proximal and distal ends, the proximal end is connectable to the at least one light source; and a diffuser element having an active length, wherein the distal end of the light guide extends into the diffuser element perpendicularly with respect to the input face, wherein the diffuser element emits light laterally with respect to the longitudinal axis over the active length, wherein the diffuser element has at least one diffuser base body that comprises a matrix with at least one scattering element, wherein the diffuser element is enclosed at least in sections on a solid encapsulation, wherein the solid encapsulation is configured as a multipart or multilayer structure comprising at least a first and a second encapsulating tube and/or layer, wherein the second encapsulating tube and/or layer surrounds at least in part the first encapsulating tube and/or layer, wherein the first encapsulating tube and/or layer is transparent, wherein the second encapsulating tube and/or layer is translucent or scattering, and wherein the second encapsulating tube and/or layer surrounds the first encapsulating tube and/or layer and the refractive index of the second encapsulating tube and/or layer is higher than the refractive index of the first encapsulating tube and/or layer.

2. The illumination system of claim 1, wherein the solid encapsulation comprises at least three encapsulating tubes and/or layers.

3. The illumination system of claim 1, further comprising at least one feature selected from a group consisting of: the at least one scattering element being aligned parallel the longitudinal axis, the at least one scattering element being angled with respect to the longitudinal axis, the at least one scattering element being a spiral with a constant pitch around the longitudinal axis, the at least one scattering element being a helical around the longitudinal axis, a device configured to homogenize an emission intensity along the longitudinal axis is provided, a reflector face at the distal end that reflects light at least partially, an intensity distribution of lateral emission that deviates by at most ±50% from an average lateral emission intensity, an intensity distribution of lateral emission that deviates by at most ±30% from an average lateral emission intensity, an intensity distribution of lateral emission that deviates by at most ±5% from an average lateral emission intensity, and any combinations thereof.

4. The illumination system of claim 1, wherein the at least two encapsulating tubes and/or layers comprise a first encapsulating tube that encloses the matrix at least in sections or fully, and wherein the first encapsulating tube is transparent and/or has a refractive index lower than a refractive index of the matrix.

5. The illumination system of claim 1, wherein the first encapsulating tube comprises a transparent borosilicate glass, and/or wherein the second encapsulating tube comprises a white glass or consists of a ring-shaped arrangement of individual white glass rods.

6. The illumination system of claim 4, wherein the at least two encapsulating tubes and/or layers further comprise a third encapsulating tube and/or layer that encloses the second encapsulating tube and/or layer at least in sections or fully, and wherein the third encapsulating tube is transparent.

7. The illumination system of claim 1, wherein the at least two encapsulating tubes and/or layers comprise at least one encapsulating tube of X-ray opaque glass.

8. The illumination system of claim 1, wherein the matrix and the solid encapsulation is a closed, sealed composite without cavities or air bubbles.

9. The illumination system of claim 1, wherein the diffuser element comprises glass.

10. The illumination system of claim 1, wherein the diffuser element, the matrix, the at least one scattering element, and the at least two encapsulating tubes and/or layers comprise glass and are fused to one another to form a continuous body.

11. The illumination system of claim 1, wherein the at least one light source comprises source selected from a group consisting of a laser light source, a semiconductor-based light source, a light-emitting diode (LED), a laser diode (LD), and a laser.

12. The illumination system of claim 1, further comprising a reflector face at the distal end, the reflector terminating the at least one diffuser base body and reflecting light directly and/or diffusely, the reflector face being formed as a sputtered or vapor-deposited dielectric reflection layer on the distal end.

13. The illumination system of claim 12, wherein the reflector face comprises a plurality of layers, the plurality of layers providing a maximum reflectivity at a wavelength of light emitted by the at least one light source.

14. The illumination system of claim 13, wherein the maximum reflectivity has a first maximum at an application wavelength and a second maximum at a wavelength differing from the application wavelength, and wherein the first and second maximums have a reflectivity greater than 95%.

15. The illumination system of claim 12, wherein the reflector face has an angle of less than 90° with respect to the longitudinal axis and reflects light with a larger numerical aperture than light which impinges thereon.

16. The illumination system of claim 1, further comprising a transparent sleeve made glass or plastic at a connecting zone between the light guide and the diffuser base body, a translucent or partially absorbent encapsulation is between the transparent sleeve and an outer cladding of the light guide, wherein the translucent or partially absorbent encapsulation is formed from a polymer in which scattering particles are incorporated.

17. The illumination system of claim 16, wherein the translucent or partially absorbent encapsulation is a tubing section, a shrink tubing section and/or a re-coating polymer, into which scattering particles is introduced.

18. A method for producing an illumination system comprising the steps of:

providing a multiplicity of light guide rods consisting of a glass having a refractive index n1 and/or n1';

providing at least one scattering rod consisting of a glass or a glass ceramic having scattering centers;

arranging the multiplicity of light guide rods and the at least one scattering rod so that longitudinal axes of the multiplicity of light guide rods and the at least one scattering rod extend parallel to one another to define a preform;

providing at least a first and a second encapsulating tube and/or layer surrounding the at least one scattering rod;

heating the preform; and drawing the preform to obtain a diffuser base body, wherein the second encapsulating tube and/or layer surrounds the first encapsulating tube and/or layer and the refractive index of the second encapsulating tube and/or layer is higher than the refractive index of the first encapsulating tube and/or layer.

* * * * *